(12) United States Patent
Dorato et al.

(10) Patent No.: US 9,321,706 B2
(45) Date of Patent: Apr. 26, 2016

(54) RECOVERY OF MONOMERS

(75) Inventors: Margarita Dorato, Clermont-Ferrand (FR); Pierre Kiener, Clermont-Ferrand (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 288 days.

(21) Appl. No.: 14/113,374

(22) PCT Filed: Apr. 17, 2012

(86) PCT No.: PCT/EP2012/056974
§ 371 (c)(1),
(2), (4) Date: Dec. 20, 2013

(87) PCT Pub. No.: WO2012/143341
PCT Pub. Date: Oct. 26, 2012

(65) Prior Publication Data
US 2014/0114111 A1 Apr. 24, 2014

(30) Foreign Application Priority Data
Apr. 22, 2011 (FR) ..................... 11 53493

(51) Int. Cl.
*C07C 7/10* (2006.01)
*C07C 7/04* (2006.01)
*C07C 7/11* (2006.01)
*B01D 53/14* (2006.01)

(52) U.S. Cl.
CPC .............. *C07C 7/10* (2013.01); *B01D 53/1487* (2013.01); *C07C 7/04* (2013.01); *C07C 7/11* (2013.01); *B01D 2252/205* (2013.01); *B01D 2256/24* (2013.01); *B01D 2257/7022* (2013.01); *B01D 2257/7027* (2013.01)

(58) Field of Classification Search
None
See application file for complete search history.

(56) References Cited

U.S. PATENT DOCUMENTS 2,409,250 A   10/1946   Cannon et al.

FOREIGN PATENT DOCUMENTS

| GB | 570870 A | 7/1945 |
| GB | 2063291 A | 6/1981 |
| WO | 8903009 A1 | 4/1989 |

OTHER PUBLICATIONS

FR 1153493, French Search Report, dated Nov. 29, 2011, 6 pages.

*Primary Examiner* — Tam M Nguyen
(74) *Attorney, Agent, or Firm* — Dickinson Wright PLLC

(57) ABSTRACT

Process for the recovery of diene or vinylaromatic monomers from a gas stream, including bringing the gas stream into contact, in an extraction column (C1), with an organic extraction solvent, which absorbs the monomer, and stripping or desorption with an inert gas in (C1), by feeding, at the bottom of (C1) below the feeding of the monomers, a stream of inert gas, a liquid stream having the extraction solvent and the monomer recovered at the bottom of (C1) and an exiting gas stream recovered at the top of (C1), then within a second recovery column C2,recovery of the monomer, wherein the monomer is separated from the extraction solvent by distillation fed with the liquid stream recovered at the bottom of (C1), a stream comprising concentrated monomer(s) recovered at the top of (C2) and a liquid stream having the extraction solvent recovered at the bottom of (C2) and then recycled to the top of (C), the monomer or monomers being dienes, vinylaromatic compounds, or isobutene.

Figure 1:
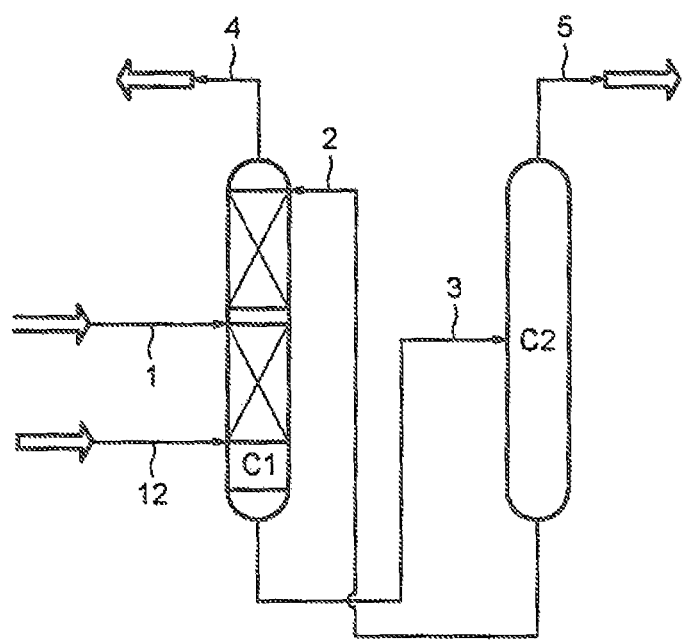

10 Claims, 5 Drawing Sheets

RECOVERY OF MONOMERS

CROSS-REFERENCE TO PRIOR APPLICATIONS

This application claims the benefit of the filing date of PCT Application No. PCT/EP2012/056974, filed Apr. 17, 2012, which claims the benefit of the filing date of the French application no. 1153493, filed Apr. 22, 2011, each document being incorporated by reference in its entirety.

The present invention relates to a process for the recovery of diene or vinylaromatic monomers from a gas stream, this recovery process comprising a stage of extraction by bringing the gas stream into contact with an organic extraction solvent, in order to absorb the monomer or monomers, and then a stage of recovery in which the monomer or monomers are separated from the extraction solvent, the latter subsequently being recycled in order to feed the extraction stage.

In the field of the extraction and/or recovery of hydrocarbons present in a dilute gas stream, there exists mainly four types of extraction process: cryogenic separation processes, processes of separation by selective membranes, processes of adsorption/desorption of the monomers on selective supports and processes of absorption of the monomers in selective solvents.

Cryogenic separation processes are well known to a person skilled in the art but these processes are expensive and require devices which make it possible to operate at very low temperature and often at high pressure.

The extraction of the monomers from a gas stream by selective membranes has been provided as an alternative to cryogenic separation. For example, Patent U.S. Pat. No. 5,769,927 describes a process for recovery of monomers from the purge gas in three stages; condensation, flash evaporation and membrane separation. However, the first two stages require, however, a cryogenic treatment at very low temperatures (−60° C.) and at high pressures (35 bar).

The extraction of the monomers from a gas stream by adsorption/desorption has also been studied as an alternative to cryogenic separation. For example, Patent EP 1 302 478 describes the recovery of monomers by adsorption and desorption on silica or alumina gel. The recovery of the monomer is carried out by a PSA (Pressure Swing Adsorption) process. However, this type of process nevertheless generally requires low pressures, of the order of 0.1 bar, for the desorption of the monomer.

Furthermore, the use of the selective membranes or adsorbent supports might result in the homopolymerization of some monomers.

The separation of the light, hydrocarbons from a gas stream by using extraction solvents is also known, in particular for recovery of methane, ethane, ethylene or propylene.

Thus, there exists many industrial plants which make possible the fractionation of gas feedstocks to give a residual gas.

Thus, the document U.S. Pat. No. 2,409,250 discloses a process for separating butadiene from a gas mixture comprising butadiene arid hydrocarbons. This process comprises a stage of purification of the mixture with a solvent, in order to obtain a solution comprising the butadiene and a gas substantially free from butadiene, and of distilling the solution in order to separate the butadiene, The document WO 89/03009 also discloses a process for separating compounds from a stream of hydrocarbon gases, in particular unsaturated hydrocarbons, by bringing the stream of hydrocarbon gases into countercurrent contact, in a separation column, with a solvent, and a stage of recovery of the depleted solvent from the enriched solvent resulting from the bottom of the separation column.

However, there still exists a need to recover diene monomers or other monomers with which these diene monomers are sometimes copolymerized to prepare elastomers, which would be present in gas streams, in a simple, economical, flexible and multipurpose way, with in addition a purity such that they can be directly used in polymerization, in particular for the manufacture of tyres.

A person skilled in the art knows that the purity of a monomer is a determining factor in envisaging its use in polymerization. In a gas stream, impurities which are more or less harmful to the polymerization may be present.

Three major families of impurities which are more or less harmful to the polymerizations described above can be present in the gas streams comprising the said monomers: (I) gases, such as carbon dioxide, carbon monoxide and oxygen, (II) organic derivatives having one or more double bonds, such as oligomers of the target monomer, and (III) derivatives carrying a heteroatom, such as oxygen, sulphur or nitrogen, for example water, aldehydes, acetals, alcohols, ketones, ethers, amines and thiols.

These impurities may be harmful to the yield of the polymerization, generate side reactions which detrimentally affect She properties of the final product, reduce the activity of the catalyst, which would necessitate a greater amount, or even inhibit any reaction.

Mention may be made, by way of example, of the effect certain impurities in the polymerization of cis-1,4-polyisoprene prepared based on a transition metal: 10 ppm of carbon dioxide in the isoprene is sufficient to inhibit the polymerization. Protic impurities, such as water or ethanol have to be compensated for by an excess of the catalyst in order to prevent a decrease in the activity. Thus, it is observed, under identical polymerization conditions, that the presence of 15 ppm of water in isoprene lowers the conversion by 10 points.

It is because of this that it is important to reduce to a minimum the content of these impurities in the monomer during the recovery phase, in order to simplify, indeed even to dispense with, subsequent purification stages.

The Applicant Company has developed a recovery process which applies to diene monomers and to some monomers with which these diene monomers are sometimes polymerized to prepare elastomers, in particular of tyre grade, such as vinylaromatic monomers or isobutene, and which introduces a solution to the problem stated above.

Thus, a subject-matter of the invention is a process for the recovery of one or more monomers from a gas stream, comprising the following stages:

within one and the same first extraction column C1, a) a stage of extraction by bringing the gas stream into contact, in an extraction column C1, with art organic extraction solvent, in which the said extraction solvent absorbs the said monomer or monomers, and b) a stage of stripping or desorption with an inert gas in the extraction column C1 by feeding, at the bottom of the column C1 and below the feeding of the gas stream laden with monomers, with a stream of inert gas, preferably molecular nitrogen or a gas stream enriched in molecular nitrogen, a liquid stream comprising the extraction solvent and the monomer or monomers being recovered at the bottom of the column C1 and an exiting gas stream being recovered at the top of the column C1, then within a second recovery column C2, c) a stage of recovery of the said monomer or monomers, in which the said monomer or monomers are separated from the extraction solvent by distillation in a recovery column C2 fed with the liquid stream recovered at the bottom of the column C1, a stream comprising concentrated monomer or monomers being recovered at the top of the column C2 and a liquid stream comprising the extraction solvent being recovered at the bottom of the column C2 and then recycled to the top of the column C1, the monomer or monomers being chosen from dienes, vinylaromatic compounds and isobutene.

In particular, the monomer or monomers recovered by the process according to the invention can be chosen from isoprene, butadiene, isobutene and styrene.

The extraction solvent is generally chosen from aliphatic, cycloaliphatic and aromatic hydrocarbons having from 5 to 20 carbon atoms, preferably having from 6 to 15 carbon atoms and more preferably having from 6 to 10 carbon atoms. Use will preferably be made of a solvent which is not an impurity for the polymerization of the elastomers used in the manufacture of tyres. Mention may he made, as a particularly preferred extraction solvent, of n-hexane, hexane isomer fractions, cyclohexane, n-heptane, heptane isomer fractions, methylcyclohexane and toluene.

The process according to the invention can also comprise a stage of condensation of the exiting gas stream recovered at the top of the column C1 followed by a separation stage in order to recover, on the one hand, a gas purge and, on the other hand, a solution of condensed hydrocarbons comprising extraction solvent and monomer or monomers, the said solution being recycled at the top of the column C1.

The liquid stream comprising the extraction solvent and monomer or monomers recovered at the bottom of the column C1 can be heated in a heat exchanger E3 by the liquid stream comprising the extraction solvent recovered at the bottom of the column C2.

The process according to the invention can also comprise a stage of condensation of the stream comprising concentrated monomer or monomers recovered at the top of the column C2, followed by a separation stage in order to recover, on the one hand, noncondensable compounds and, on the other hand, a stream of monomer(s), a portion of the stream of monomer(s) being reinjected at the top of the column C2.

The ratio of the flow rate of stream of monomer(s) reinjected at the top of the column C2 to the flow rate of stream of monomer(s) not reinjected at the top of the column C2 is known as reflux ratio. The reflux ratio is generally between 0.001 and 50.

The noncondensable compounds can be recycled at the bottom of the column C1.

A portion of the liquid stream comprising the extraction solvent recovered at the bottom of the column C2 can be evaporated by an exchanger E5 and reinjected at the bottom of the column C2.

According to a specific embodiment, the liquid stream comprising the extraction solvent and monomer(s) recovered at the bottom of the column C1 is subjected to a separation stage in order to recover, from the said solvent, a portion of the nancondensable compounds, the said noncondensable compounds being reintroduced at the bottom of the column C1.

According to another specific embodiment, a portion of the liquid stream comprising the extraction solvent and monomer or monomers recovered at the bottom of the column C1 is evaporated in a heat exchanger E6 and is reintroduced at the bottom of the column C1.

The monomers obtained by the process according to the invention can advantageously be used for the synthesis of polymers which can themselves be used in the manufacture of tyres.

Figure 2:
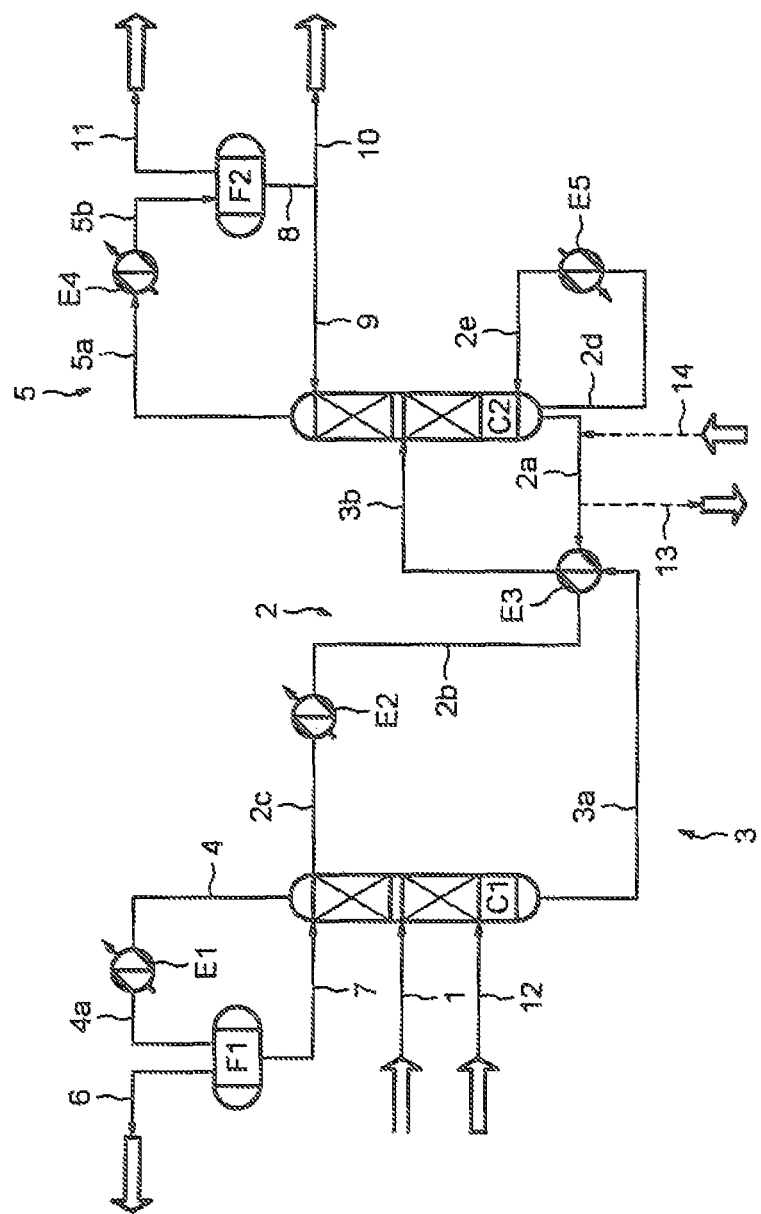
Figure 3:
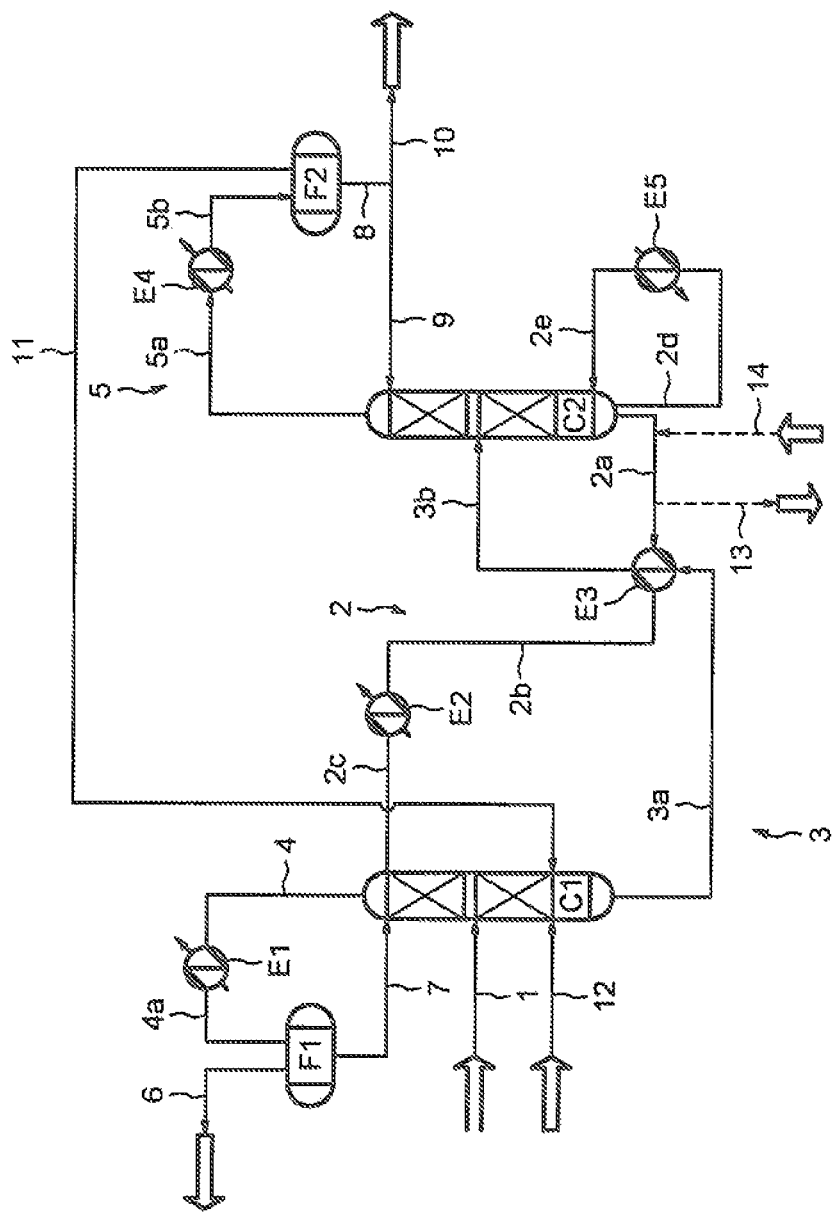
Figure 4:
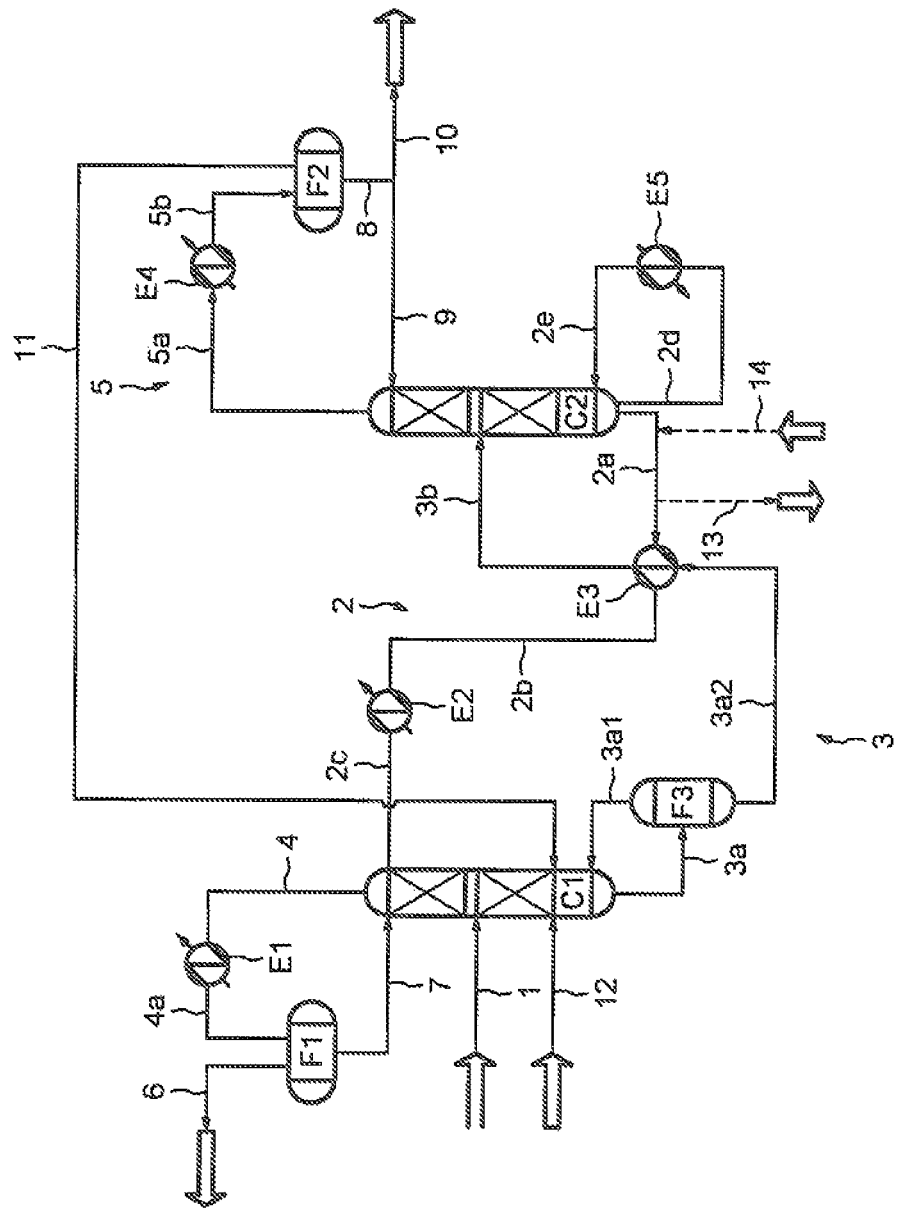
Figure 5:
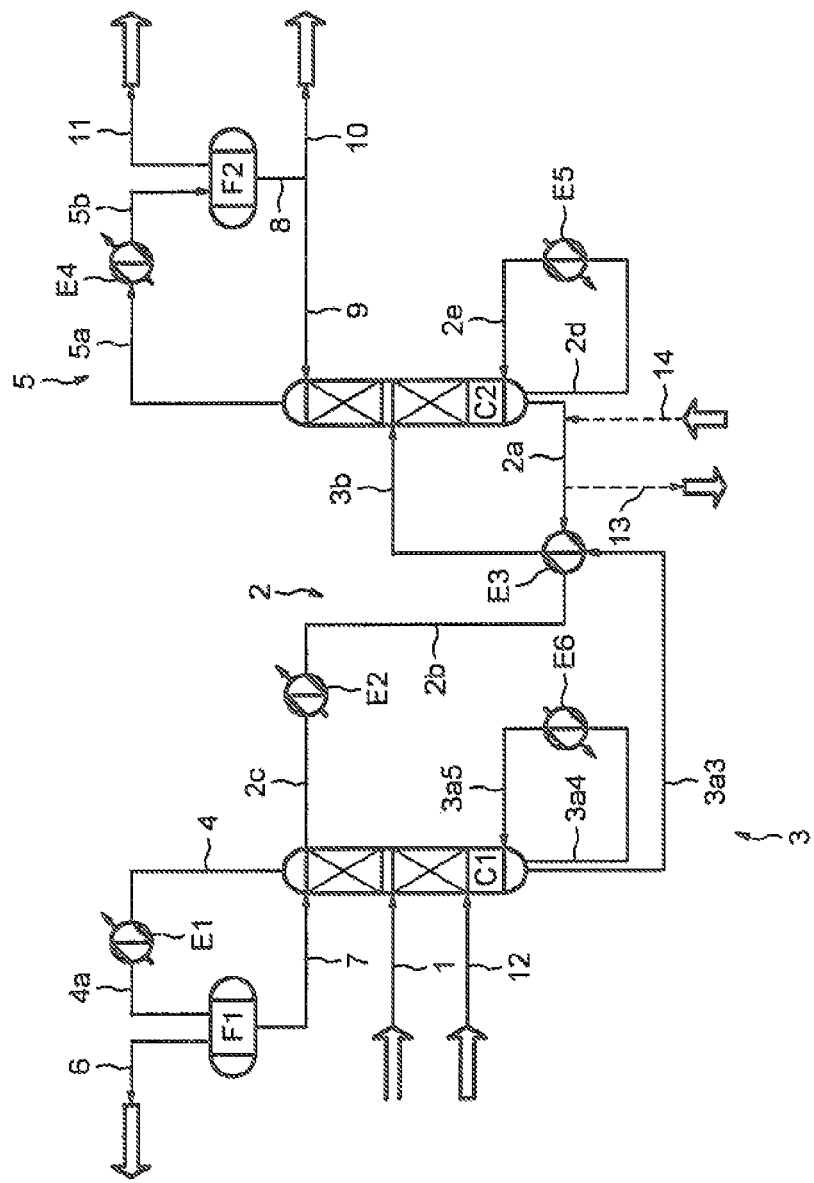

Other advantages and characteristics will become apparent on examining the detailed description of embodiments of the invention, which are in no way limiting, and the appended drawings, in which:

FIG. 1 diagrammatically illustrates the general process according to the invention;

FIG. 2 diagrammatically illustrates an embodiment of the process according to the invention;

FIG. 3 diagrammatically illustrates another embodiment of the process according to the invention, in which in particular the noncondensable compounds recovered after the distillation are recycled in the extraction column C1;

FIG. 4 diagrammatically illustrates another embodiment of the process according to the invention;

FIG. 5 diagrammatically illustrates another embodiment of the process according to the invention.

The process according to the invention has been diagrammatically represented in FIG 1.

The gas stream 1 from which the monomers are recovered can originate, without implied limitation, from a purge subsequent to a polymerization stage, for example a gas purge from a loop for cooling the polymerization reaction by evaporation, from a stage of concentrating polymer solution, for example, any stage of removal of the unreacted monomers and reaction solvent from a polymer solution, for example with an entrainment agent, such as nitrogen, from a purge subsequent to a stage of purification of the monomers, for example from a purification by entrainment with a stripping agent, or recovery of the gas phase from an azeotropic distillation column or of a bioreactor, such as a fermenter of a photobioreactor.

The gas stream 1 generally comprises, as main components but without the least limitation., molecular nitrogen, carbon monoxide, carbon dioxide, molecular oxygen, argon, molecular hydrogen, water and hydrocarbons, including the monomer or monomers to be recovered. The gas stream 1 can comprise, as minor components, derivatives carrying a heteroatom, such as oxygen, sulphur or nitrogen, for example water, aldehydes, acetals, alcohols, ethers, ketones, amines or thiols. It can also comprise other hydrocarbons, including the polymerization solvent.

The gas stream 1 feeds the middle of the extraction column C1, in which it is brought into contact with the extraction solvent 2 fed at the column top. The solvent absorbs the said monomer or monomers. A stream of inert gas 12, such as molecular nitrogen or a stream of gas enriched in molecular nitrogen, is fed at the bottom of the column C1. This inert gas facilitates the desorption of the light compounds which are potentially harmful to the polymerization, such as molecular oxygen, carbon monoxide, carbon dioxide and water, inter alia. Thus, the column C1 exhibits an absorption region above the level of feeding the gas stream 1, in which the heavy components of the gas stream 1 are transferred from the gas phase to the liquid phase in order to enrich this phase in monomer(s), and a desorption region below the level of feeding the gas stream 1, in which some components of the liquid phase are transferred to the gas phase in order to deplete the said liquid phase in the light components, such as carbon dioxide, carbon monoxide, molecular oxygen and water, inter alia.

There are then recovered, at the bottom of the column C1, a liquid stream 3 comprising mainly the extraction solvent and monomer or monomers and, at the top of the column C1, an exiting gas stream 4. The exiting gas stream 4 has a very low monomer content. It essentially comprises gases present in the stream 1, solvent and a reduced amount of the monomer or monomers, and also the inert gas originating from the stripping. The recovery efficiency of the column C1 can reach 99.99%, that is to say that the liquid stream 3 recovered at the bottom of the column C1 can comprise up to 99.99% by weight of the monomer or monomers initially present in the gas stream 1.

The liquid stream 3 comprising the extraction solvent and monomer or monomers is then conveyed to the column C2.

The monomer or monomers are separated from the extraction solvent by distillation in the recovery column C2. The concentrated stream of monomer(s) 5 is recovered at the top of the column C2. The content of monomer(s) in the concentrated stream of monomer(s) 5 can reach 99.99% by weight. The liquid stream 2 comprising the extraction solvent is recovered at the bottom of the column C2 and is recycled at the top of the column C1.

An economical and flexible embodiment of the process according to the invention has been represented diagrammatically in FIG. 2. The references from FIG. 1 have been transferred onto this FIG. 2. The liquid stream 3a is heated in a heat exchanger E3 by the liquid stream 2a; the heated liquid stream 3b, which exits from the exchanger E3, is directed to the column C2. In the same way, the liquid stream 2a recovered at the bottom of the column C2 is directed to the exchanger E3 and the liquid stream 2b which exits cooled from the exchanger E3 is directed to an exchanger E2, and the liquid stream 2c which exits from the exchanger E2 is conditioned in temperature by the latter and is introduced at the top of the column C1.

The exiting gas stream 4 is recovered at the top of the column C1. It essentially comprises gases present in the stream 3, solvent and a reduced amount of monomer(s), and also inert gas originating from the stripping. It is subjected to a condensation stage in a condenser E1, in order to recover possible hydrocarbons entrained by the gas phase. This gas stream 4a is then separated in the tank F1, in order to recover, on the one hand, a gas purge 6 comprising the majority of the gases present in the stream 1, a reduced amount of the solvent and possible traces of monomer(s) and, on the other hand, a liquid stream 7 of condensed hydrocarbons comprising an extraction solvent and a reduced amount of monomer(s). The liquid stream 7 is recycled at the top of the column C1.

In the same way, the concentrated stream of monomer(s) 5a recovered at the top of the column C2 is completely or partially condensed in a condenser E4, in order to give a gas stream 5b which is separated in the tank F2, in order to recover, on the one hand, noncondensable compounds 11 originating from the gases dissolved in the liquid stream 3a and, on the other hand, a stream of monomer(s) 8. The stream of monomer(s) possibly comprises, in addition to the monomer or monomers, a small amount of molecular nitrogen, a small amount of extraction solvent and possibly traces of gases, such as carbon dioxide or molecular oxygen, inter alia. A portion 9 of the stream of monomer(s) is reinjected, providing the reflux at the top of the column C2, the other portion 10 being the distillate. The reflux ratio, the ratio of the flow rate of the stream 9 to the flow rate of the stream 10, is defined in order to achieve a purity of monomer(s) of the stream 10 which can reach 99.99%. The reflux ratio is generally between 0.001 and 50. This value can vary according to the dimensioning of the column C2, as is known to a person skilled in the art.

A portion 2d of the liquid stream comprising the extraction solvent recovered at the bottom of the column C2 is evaporated by an exchanger E5 and is reinjected at the bottom of the column C2, which provides the reboiling in the column. The reboil ratio, the ratio of the flow rate of the evaporated part of the stream 2e to the flow rate of the stream 2a, is set as a function of the concentration of monomer(s) desired an the stream 2a at the bottom of the column C2. The reboil ratio is generally between 0.01 and 30. This value can vary according to the dimensioning of the column C2, as is known to a person skilled in the art.

The column C2 conventionally exhibits a concentration region above the level of feeding the liquid stream 3b, in which the vapour generated in the reboiler E3 is enriched in monomer, and a depletion region below the level for feeding the liquid stream 3b, in which the liquid of the stream 9 originating from the reflux is depleted in monomer(s).

It is possible to introduce fresh extraction solvent 14 at the level of the liquid stream 2a line in order to be able to contribute solvent according to the requirements.

It is also possible to provide a purge of heavy components 13 at the level of the liquid stream 2a line. This purge stream can be obtained by any appropriate device, including those which make possible the purification of the extraction solvent, which can then be injected again at the point 14.

An embodiment of the process according to the invention has been represented diagrammatically in FIG. 3. The references from FIG. 2 have been transferred onto this FIG. 3.

In this embodiment, the noncondensable compounds 11 are recycled at the bottom of the column C1.

An embodiment of the process according to the invention has been represented diagrammatically in FIG. 4. The references from FIG. 3 have been transferred onto this FIG. 4.

The liquid stream 3a comprising the extraction solvent and monomer or monomers recovered at the bottom of the column C1 is separated in a tank F3 in order, on the one hand, to obtain a portion of the noncondensable compounds 3a1, which are reintroduced at the bottom of the column C1, and, on the other hand, to recover a liquid stream 3a2, comprising the extraction solvent and monomer or monomers, which is conveyed to the exchanger E3.

An embodiment of the process according to the invention has been represented diagrammatically in FIG. 5. The references from FIG. 2 have been transferred onto this FIG. 5.

A portion 3a4 of the liquid stream comprising the extraction solvent and monomer or monomers recovered at the bottom of the column C1 is evaporated by an exchanger E6 in order to form a stream 3a5 which is reinjected at the bottom of the column C1, which provides optional reboiling in the column. The reboil ratio, ratio of the flow rate of the evaporated portion of the stream 3a5 to the flow rate of the stream 3a4, is set as a function of the concentration of light components other than the monomer or monomers which is desired in the stream 3a3 at the bottom of the column C1. The reboil ratio is generally between 0.01 and 30. This value can vary according to the dimensioning of the column C1, as is known to a person skilled in the art. The stream 3a3 at the bottom of the column C1 is sent to the exchanger E3.

In all of the embodiments of the invention, the quality of the monomer or monomers obtained depends on the conditions employed in the columns C1 and C2: temperatures, pressures, choice of the extraction solvent as a function of the nature of the gas stream, the ratio of flow rate of gas stream to the solvent stream, reflux ratio, reboil ratio or number of plates. The choices of these parameters give a high degree of efficiency and flexibility to the process according to the invention. The temperatures can be between −30° C. and 200° C. and the pressures can be between 0.5 and 10 bar. The number of the plates can be between 2 and 50.

The invention is illustrated by the following examples.

EXAMPLE 1

A process for the recovery of isoprene according to the invention is studied by modelling using Aspen Plus™ software. The process is carried out according to the embodiment of FIG. 4. The extraction solvent used is cyclohexane.

The conditions for the operation of the extraction column C1 are given in Table 1.

TABLE 1

| | |
|---|---|
| Number of theoretical plates | 20 |
| Temperature (° C.) | 10 |
| Pressure (bar) | 2 |
| Ratio of flow rate by weight of cyclohexane to flow rate by weight of inlet gas stream | 3 |

The operating conditions for the recovery column C2 are given in Table 2.

TABLE 2

| | |
|---|---|
| Number of theoretical plates | 20 |
| Feed plate | 17 |
| Pressure (bar) | 2.5 |
| Reflux ratio | 1.36 |
| Reboil ratio | 3 |

The compositions of the incoming and outgoing streams are given in Table 3.

TABLE 3

| | Incoming streams | | | Outgoing streams | |
|---|---|---|---|---|---|
| | Line-reference | | | | |
| | 1 | 12 | 14 | 6 | 10 |
| | Description | | | | |
| Component | Inlet gas stream | Molecular nitrogen | Extra solvent | Gas purge | Purified isoprene |
| | Fraction by weight | | | | |
| $N_2$ | 0.504 | 1 | | 0.641 | 0.002 |
| $O_2$ | 0.088 | | | 0.07 | 0 |
| $CO_2$ | 0.286 | | | 0.228 | 0 |
| Ar | 0.009 | | | 0.007 | 0 |
| Isoprene | 0.112 | | | 0.001 | 0.998 |
| Cyclohexane | | | 1 | 0.051 | 0 |
| Water | 0.001 | | | 0.001 | 0 |
| | Ratio of flow rates | | | | |
| w/wI0 | 8.9 | 2.7 | 0.6 | 11.2 | 1.0 |
| w/wGS0 | 1.0 | 0.3 | 0.1 | 1.3 | 0.1 | w/wI0: flow rate by weight of the stream/flow rate by weight of isoprene in the inlet gas stream
w/wFG₀: flow rate by Weight of the stream/flow rate by weight of the inlet gas stream

EXAMPLE 2

A process for the recovery of isoprene according to the invention is studied by modelling using Aspen Plus™ software. The process is carried out according to the embodiment of FIG. 4. The extraction solvent used is cyclohexane.

The conditions for the operation of the extraction column C1 are given in Table 4.

TABLE 4

| | |
|---|---|
| Number of theoretical plates | 20 |
| Temperature (° C.) | 10 |
| Pressure (bar) | 2 |
| Ratio of flow rate by weight of cyclohexane to flow rate by weight of inlet gas stream | 4 |

The operating conditions for the recovery column C2 are given in Table 5.

TABLE 5

| | |
|---|---|
| Number of theoretical plates | 20 |
| Feed plate | 17 |
| Pressure (bar) | 2.5 |
| Reflux ratio | 3.1 |
| Reboil ratio | 0.08 |

The compositions of the incoming and outgoing streams are given in Table 6.

TABLE 6

| | Incoming streams | | | Outgoing streams | |
|---|---|---|---|---|---|
| | Line-reference | | | | |
| | 1 | 12 | 14 | 6 | 10 |
| | Description | | | | |
| Component | Inlet gas stream | Molecular nitrogen | Extra solvent | Gas purge | Purified isoprene |
| | Fraction by weight | | | | |
| $N_2$ | 0.504 | 1 | | 0.642 | 0.002 |
| $O_2$ | 0.088 | | | 0.07 | 0 |
| $CO_2$ | 0.286 | | | 0.228 | 0 |
| Ar | 0.009 | | | 0.007 | 0 |
| Isoprene | 0.112 | | | 0 | 0.981 |
| Cyclohexane | | | 1 | 0.051 | 0.017 |
| Water | 0.001 | | | 0.001 | 0 |
| | Ratio of flow rates | | | | |
| w/wI0 | 8.9 | 2.7 | 0.6 | 11.2 | 1.0 |
| w/wFG0 | 1.0 | 0.3 | 0.1 | 1.3 | 0.1 | w/wI0: flow rate by weight of the stream/flow rate by weight of isoprene in the inlet gas stream
w/wFG₀: flow rate by weight of the stream/flow rate by weight of the inlet gas stream

The invention claimed is:

1. A process for the recovery of one or more monomers from a gas stream, comprising the following stages:
within a first extraction column C1,
a) a stage of extracting by bringing the gas stream into contact, in an extraction column (C1), with an organic extraction solvent, wherein said extraction solvent absorbs said monomer or monomers, and
b) a stage of stripping or desorbing with an inert gas in the extraction column (C1), by feeding, at the bottom of the column (C1) and below the feeding of a gas stream laden with monomers, a stream of the inert gas,
recovering a liquid stream comprising the extraction solvent and the monomer or monomers at the bottom of the column (C1) and recovering an exiting gas stream at the top of the column (C1), then
within a second recovery column C2,
c) a stage of recovering of said monomer or monomers, wherein said monomer or monomers are separated from the extraction solvent by distillation in a recovery column (C2) fed with the liquid stream recovered at the bottom of the column (C1), recovering a stream comprising concentrated monomer(s) at the top of the column (C2) and recovering a liquid stream comprising the extraction solvent at the bottom of the column (C2) and then recycling said liquid stream to the top of the column (C1),
wherein the monomer or monomers are selected from the group consisting of dienes, vinylaromatic compounds and isobutene.

2. The process according to claim 1, wherein the monomer or monomers are selected from the group consisting of isoprene, butadiene, isobutene and styrene.

3. The process according to claim 1, wherein the extraction solvent is selected from the group consisting of aliphatic, cycloaliphatic and aromatic hydrocarbons having from 5 to 20 carbon atoms.

4. The process according to claim 3, wherein the extraction solvent is selected from the group consisting of n-hexane, hexane isomer fractions, cyclohexane, n-heptane, heptane isomer fractions, methylcyclohexane and toluene.

5. The process according to claim 1, further comprising a stage of condensation of the exiting gas stream recovered at the top of the column (C1) followed by a separation stage in order to recover, on the one hand, a gas purge and, on the other hand, a solution of condensed hydrocarbons comprising extraction solvent and monomer or monomers, and recycling said solution at the top of the column (C1).

6. The process according to claim 1, further comprising heating the liquid stream comprising the extraction solvent and monomer or monomers recovered at the bottom of the column (C1) in a heat exchanger E3 by the liquid stream comprising the extraction solvent recovered at the bottom of the column (C2).

7. The process according to claim 1, further comprising a stage of condensation of the stream comprising concentrated monomer(s) recovered at the top of the column (C2), followed by a separation stage in order to recover, on the one hand, noncondensable compounds and, on the other hand, a stream of monomer(s), and reinjecting a portion of the stream of monomer(s) at the top of the column (C2).

8. The process according to claim 7, further comprising recycling the noncondensable compounds at the bottom of the column (C1).

9. The process according to claim 1, further comprising subjecting the liquid stream comprising the extraction solvent and monomer or monomers recovered at the bottom of the column (C1) to a separation stage in order to separate, from the said solvent, a portion of the noncondensable compounds, and reintroducing said noncondensable compounds at the bottom of the column (C1).

10. The process according to claim 1, further comprising evaporating a portion of the liquid stream comprising the extraction solvent and monomer or monomers recovered at the bottom of the column (Cl) in a heat exchanger E6 and reintroducing this portion at the bottom of the column (C1).

* * * * *